April 28, 1964 P. ECKE Plant Pat. 2,398
POINSETTIA PLANT
Filed April 29, 1963
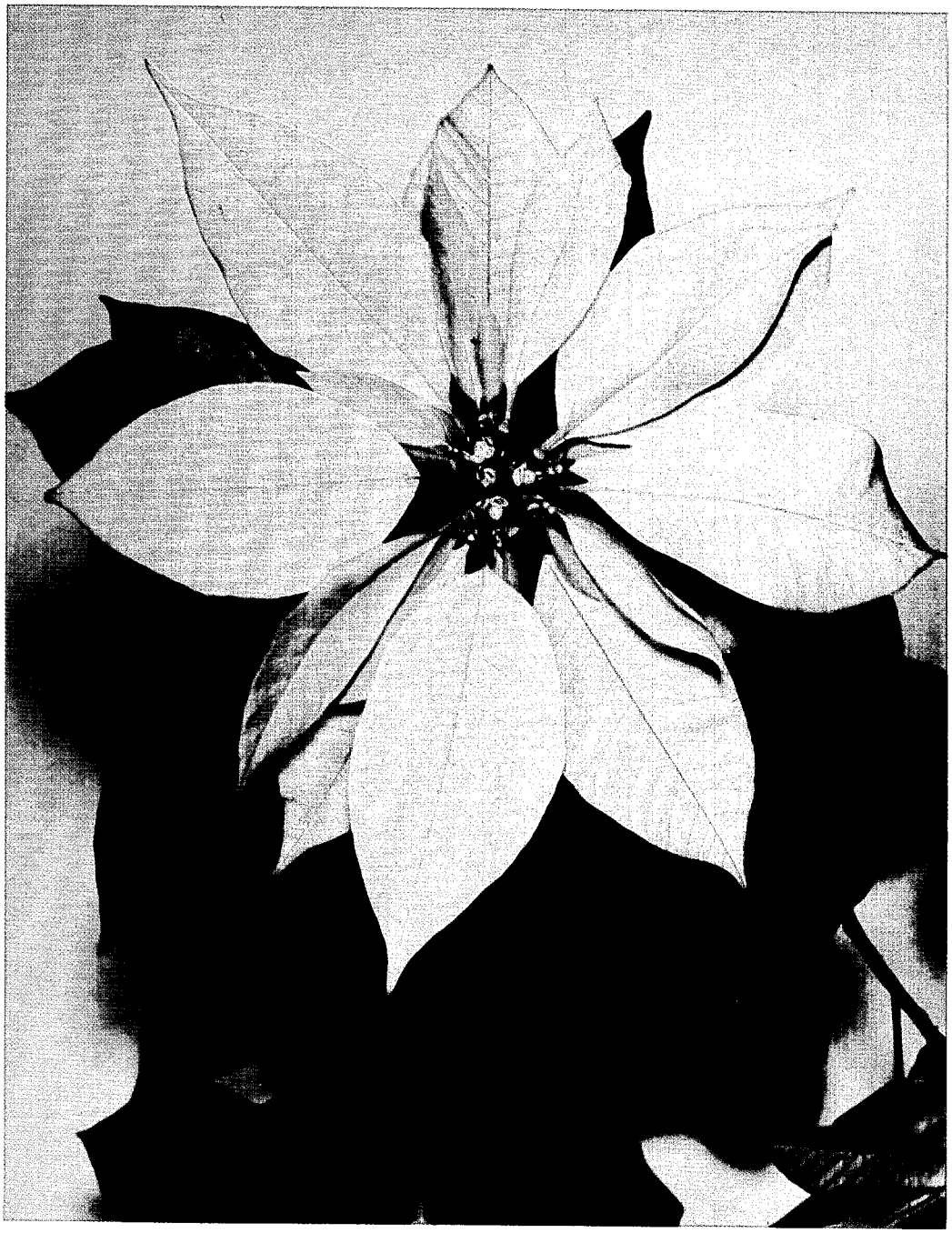
INVENTOR
PAUL ECKE
BY Wm. S. Graham
ATTORNEY United States Patent Office Plant Pat. 2,398
Patented Apr. 28, 1964

2,398
POINSETTIA PLANT

Paul Ecke, P.O. Box 488, Encinitas, Calif.
Filed Apr. 29, 1963, Ser. No. 276,679
1 Claim. (Cl. Plt.—86)

The subject of the present invention or discovery is a new and distinct variety of poinsettia plane (*Euphorbia pulcherrima*) originating as a cultivated sport.

Broadly, this new variety of poinsettia plant is distinguishable from its parent plant, as well as from other known varieties, mainly by the unusual subdued luster of a rich hue of rose pink color of its bracts, as well as the proliferation of longer and wider bracts that have unusually short petioles for a pink variety, which thereby contracts the open center of the bract involucre around an abundant, closely centered inflorescence. This new variety is also characterized by an unusually strong and stiff peduncle, which is resistant to breakage in handling and shipment, and bracts that are flexible and reasonably resistant to damage in shipment.

The accompanying illustration forming a part of this application, graphically shows this new variety in color at substantially full maturity or optimum, the illustration being substantially a full-faced view of the bract involucre.

The colors referred to herein correspond approximately with those shown in "Dictionary of Color" by Maerz and Paul (first edition, 1930) and identified by the common color names thereof, and by the plate of said color standard as recapitulated in tabulated form herein.

The following description more fully sets forth the characteristics of this new variety.

*Parentage*

In parentage this new variety was originated, discovered and cultivated by me in a cultivated area of the glass house at my experimental and growing gardens at Encinitas, California, and has been asexually reproduced by cuttings. It originated as a cultivated sport of poinsettia plant of the variety commonly designated "Gloria," which is an unpatented variety, but is well known in the trade by that name.

*Propagation*

This new variety of poinsettia plant has been asexually reproduced and cultivated by me in my propagating glass house by cuttings, and successive reproductions thereof have remained true to type, and it has shown the herein described qualities and characteristics to be permanently fixed. In asexually reproducing the new variety, it has been found satisfactory and efficient to cut pieces of stalk of softwood substantially 6 inches in length in or about the months of June, July and August, and to set one end of such cuttings in beds of sand in my propagating glass house. This new variety propagates and roots rapidly in approximately 3 weeks, in which time the cuttings are well rooted and may be transferred to individual pots. My experience has been that the optimum temperautre for such propagation and for growing this new variety under glass ranges from 62 to 65 degrees F. night temperature, the daytime temperature being warmer, such as 70 to 75 degrees F., and subject to varying conditions of light, heat, thickness of glass, cultivation, character of soil, and fertilization, pruning or pinching.

*Habits of Growth and Structure*

This new variety of poinsettia plant develops its physical growth rapidly, and is a strong vigorous grower, sending out strong and hard main stalk peduncles. It also develops a large strong growth of root structure. Under usual and normal growing conditions, whether field grown or grown under glass, this new variety grows to a height of from 3 to 4 feet. Under the usual growing conditions it will naturally produce its bract involucre in mid-November, but is exceptionally adaptable to artificial delay of optimum by reducing the growing temperature to 50 degrees F., under which condition its optimum may be delayed, and it will hold its foliage and bracts until Christmas, which is the best commercial season.

The peduncles or main stalks are of a medium dark brownish-green color and of stiff, hard and sturdy structure. At the upper free terminal or axial end of the peduncles, a node is formed from which grow pale green closely grouped short branches or stemlike spurs which bear the bract involucre and a closely centered inflorescence. The bracts are flexible and tough and resistant to bruising in handling and shipment, which together with its strong hard peduncle, make it a very satisfactory variety for efficient handling and shipment, and more particularly because it normally reaches an optimum in early or mid-November and is therefore available for an early market season, yet, as previously stated, it may also be maintained at optimum until Christmas by subjecting it to a sustained lowered temperature of 50 degrees (F.).

*Bracts*

In most of the pink varieties of poinsettia plants, the petioles of the bracts are quite long and the bracts are relatively short and narrow, thereby providing a wide-open center to the involucre. In this present new variety the bracts are unusually long and wide, and the petioles are relatively short for a pink variety, and thus cluster the involucre of bracts closely around the inflorescence. The bracts are also spread around the inflorescence with uniformity and symmetry, and because of their width and short petioles they are drawn in toward the center whereby the edges of the unusually wide bracts are relatively overlying and the bracts radiate as a wreath with a relatively small open space around the inflorescence.

The bracts are of unusual uniformity of shade of color. The coloring of the bracts is a principal differentiation of this new variety. The color may be described in non-technical terms as a rich hue of rose-pink color of subdued luster which gives an appearance which might be colloquially termed "dusty." This coloration is quite uniform throughout the individual bracts and throughout the involucre. While the bracts have the usual variation of relative size, they have an unusual regularity of shape, being generally and predominantly prolately ovate-acuminate, or broadened lanceolate. The bracts are of usual thickness and flexibility and are very resistant to bruising, making the plant very efficient for shipment. The venation of the bracts is herringbone and quite uniform.

*Inflorescence*

The inflorescence grows upon the pale green branches or spurs heretofore described as branching from the free axial end of the peduncle, and centrally of the bract involucre. The flowers of this inflorescence are closely grouped and are prominent at the rather small, open center of the involucre, and to a substantial extent, the inflorescence fills the relatively small, open center of the involucre. As in a large number of varieties of poinsettia plants, the cyathium is of pale green color, small and not prominent, and the flower growing therefrom is orange-yellow in color with a touch of crimson-red at the center.

*Foliage Leaves*

The foliage leaves are arranged around the peduncle, the nodes thereof being quite uniformly spaced. The foliage leaves are of a dark green color and the venation thereof is of the herringbone type. The shape of the foliage leaves is substantially similar to the shape of the bracts, that is, prolately ovate-acuminate, and are not of the oak-leaf type. As is common in poinsettia plants, one or two of the foliage leaves adjacent the bract involucre may, but not always, be splashed with a coloring somewhat resembling the color of the bracts, but this is not a distinguishing fixed characteristic of this new variety and may or may not appear in different plants. It is not as prevalent as in many varieties of poinsettia plants.

*Color Tabulation*

The color designations according to the color plates of said "Maerz and Paul Dictionary of Color," are recapitulated in tabular form as follows:

| Part of Plant | Common Name of Color | Dictionary of Color | | |
|---|---|---|---|---|
| | | Plate | Letter | Number |
| Peduncle | Dark brownish green | 16 | L | 8 |
| Stemlike spurs which bear the inflorescence. | Olive green | 16 | L | 1 |
| Bracts | A rich hue of rose-pink color, but of subdued luster, quite uniform throughout the area of the bracts. | 3 | J | 4 |
| Foliage leaves | Dark green | 32 | L | 9 |
| Inflorescence: | | | | |
| Cyathium | Pale green | 21 | J | 6 |
| Flowers | Orange-yellow | 10 | J | 6 |
| Center of flowers | Crimson-red | 49 | K | 3 |

Having described and illustrated my new variety of poinsettia plant, I claim:

A new and distinct variety of poinsettia plant substantially as illustrated and described, characterized by a bract involucre in which the bracts have a rich hue of rose-pink color of subdued luster, the bracts being of substantially uniform color throughout their area and being wider and longer than in known pink varieties and of generally prolately ovate-acuminate shape, said bracts being flexible but tough and resistant to bruising, the bracts growing on relatively short petioles whereby they are closely centered around the inflorescence and radiate from the central inflorescence in a wreath in which the radiating bracts have relatively overlying adjacent edges, the inflorescence at the center of the bract involucre being prominent and closely grouped.

No references cited.